US008101717B2

(12) United States Patent
Weiss et al.

(10) Patent No.: US 8,101,717 B2
(45) Date of Patent: Jan. 24, 2012

(54) USE OF TROPOELASTIN FOR REPAIR OR RESTORATION OF TISSUE

(75) Inventors: Anthony Steven Weiss, Sydney (AU); Suzanne Marie Mithieux, Sydney (AU)

(73) Assignee: The University of Sydney, New South Wales (AU)

( * ) Notice: Subject to any disclaimer, the term of this patent is extended or adjusted under 35 U.S.C. 154(b) by 149 days.

(21) Appl. No.: 12/513,798

(22) PCT Filed: Nov. 13, 2007

(86) PCT No.: PCT/AU2007/001738
§ 371 (c)(1),
(2), (4) Date: May 6, 2009

(87) PCT Pub. No.: WO2008/058323
PCT Pub. Date: May 22, 2008

(65) Prior Publication Data
US 2010/0021440 A1    Jan. 28, 2010

(30) Foreign Application Priority Data

Nov. 13, 2006 (AU) ................................ 2006906319

(51) Int. Cl.
*A61K 38/17* (2006.01)
(52) U.S. Cl. ........................................................ 530/353
(58) Field of Classification Search ......................... None
See application file for complete search history.

(56) References Cited

U.S. PATENT DOCUMENTS

| 5,223,420 | A | 6/1993 | Rabaud |
| 5,628,785 | A | 5/1997 | Schwartz |
| 5,726,040 | A | 3/1998 | Ensley |
| 5,989,244 | A | 11/1999 | Gregory et al. |
| 5,990,379 | A | 11/1999 | Gregory |
| 6,103,269 | A | 8/2000 | Wunderlich |
| 6,110,212 | A | 8/2000 | Gregory |
| 6,372,228 | B1 | 4/2002 | Gregory |
| 6,380,154 | B1 | 4/2002 | Cappello |
| 6,632,450 | B1 | 10/2003 | Gregory |
| 6,699,294 | B2 | 3/2004 | Urry |
| 6,852,834 | B2 | 2/2005 | Chilkoti |
| 7,001,328 | B1 * | 2/2006 | Barofsky et al. ................. 600/36 |
| 2003/0059841 | A1 | 3/2003 | Chilkoti |
| 2003/0166846 | A1 | 9/2003 | Rothstein |
| 2004/0013733 | A1 | 1/2004 | Chen |
| 2005/0054578 | A1 | 3/2005 | Sandberg |
| 2005/0069573 | A1 | 3/2005 | Cohn |
| 2005/0204408 | A1 | 9/2005 | Weiss |
| 2006/0194036 | A1 | 8/2006 | Miyamoto |
| 2006/0200245 | A1 | 9/2006 | Trieu |
| 2006/0204529 | A1 | 9/2006 | Keiichi |
| 2009/0169593 | A1 * | 7/2009 | Gregory et al. ................. 424/423 |

FOREIGN PATENT DOCUMENTS

| WO | 8801623 A1 | 3/1988 |
| WO | 9507095 A1 | 3/1995 |
| WO | 9523611 A1 | 9/1995 |
| WO | 9614807 A1 | 5/1996 |
| WO | 9632406 A1 | 10/1996 |
| WO | 9805685 A2 | 2/1998 |
| WO | 9834563 A1 | 8/1998 |
| WO | 9903886 A1 | 1/1999 |
| WO | 9933903 A1 | 7/1999 |
| WO | 0044394 A1 | 8/2000 |
| WO | 0050068 A2 | 8/2000 |
| WO | 0073399 A1 | 12/2000 |
| WO | 0100666 A2 | 1/2001 |
| WO | 0156595 A2 | 8/2001 |
| WO | 0178692 A2 | 10/2001 |
| WO | 0180921 A2 | 11/2001 |
| WO | 0185801 A1 | 11/2001 |
| WO | 0213854 A1 | 2/2002 |
| WO | 03086491 A2 | 10/2003 |
| WO | 03087197 A1 | 10/2003 |
| WO | 2004012678 A2 | 2/2004 |
| WO | 2004062531 A1 | 7/2004 |
| WO | 2004084968 A1 | 10/2004 |
| WO | 2004104021 A2 | 12/2004 |
| WO | 2004104043 A1 | 12/2004 |
| WO | 2005034852 A2 | 4/2005 |
| WO | 2005072223 A2 | 8/2005 |
| WO | 2005096988 A1 | 10/2005 |
| WO | 2006001806 A2 | 1/2006 |
| WO | 2006024492 A2 | 3/2006 |
| WO | 2006042310 A1 | 4/2006 |
| WO | 2006078629 A2 | 7/2006 |
| WO | 2006086404 A2 | 8/2006 |

OTHER PUBLICATIONS

Sykes & Partridge, "Salt Soluble Elastin from Lathyritic Chicks", Biochemical Journal, 1974, vol. 141, pp. 567-572.*
Koo, Otilia, et al. "Role of nanotechnolgy in targeted drug delivery and imaging: A concise review" Nanomedicine (2005) vol. 1, No. 3, pp. 193-212.
Chilkoti, A. et al, "Targeted drug delivery by thermally responsive polymers" Advanced Drug Delivery Reviews (2002), vol. 54, No. 5, pp. 613-630.
Anderson A.B.; et al. "Combination coatings unlock device potential" Medical Device Technology, vol. 16, No. 1, pp. 12-15.
Vrhovski, B.; et al; "Coacervation characteristics of recombinant human tropoelastin" Eur. J. Biochem, (1997), vol. 250, No. 1, pp. 92-98.
Spotnitz, W.D.; "Commercial fibrin sealants in surgical care" The American Journal of Surgery, (2001), vol. 182, 8S-14S.
Morikawa, T; "Tissue Sealing" The American Journal of Surgery, (2001), vol. 182, 29S-35S.
Reece, T.B.; et al, "A prospectus on tissue sealing" The American Journal of Surgery, (2001), vol. 182, 40S-44S.
Vrhovski, B.; Weiss, A; "Biochemisty of tropoelastin" European Journal of Biochemistry, (1998), vol. 258, pp. 1-18.
Okamoto, K. et al, "Characteristics of elastin peptide in coacervate states: pH effect and possible ion transport mechanism" Peptide Chemistry (1989), 27th Edition, pp. 369-374.

(Continued)

*Primary Examiner* — Suzanne M. Noakes
(74) *Attorney, Agent, or Firm* — Edward J. Baba; Bozicevic, Field & Francis LLP

(57) ABSTRACT

The present invention relates to tropoelastin and to tissue repair and restoration using elastic materials. Disclosed is a process for producing an elastic material from tropoelastin including heating a solution of tropoelastin having an alkaline pH to form an elastic material from the tropoelastin in the solution. Also disclosed are elastic materials prepared according to this process and their applications.

11 Claims, 1 Drawing Sheet

OTHER PUBLICATIONS

Lin, S, et al, "pH and thermal-dependent conformational transition of PGAIPG, a repeated hexapeptide sequence from tropoelastin" Peptides (2005), vol. 26, pp. 543-549.

Toonkool, P. et al; "Hydrophobic domains of human tropoelastin interact in a contect dependent manner" Journal of Biological Chemistry, (2001) vol. 276, No. 48, pp. 44575-44580.

Mithieux, S.M. et al; "In situ polymerization of tropoelastin in the absence of chemical cross-linking" Biomaterials (2009) vol. 30, pp. 431-435.

GenBank entry AAC98394 (http://www.ncbi.nlm.nih.gov/protein/182020).

GenBank entry CAA33627 (http://www.ncbi.nlm.nih.gov/protein/579846).

GenBank entry P15502 (http://www.ncbi.nlm.nih.gov/protein/57015272; accession date Jul. 28, 2009).

GenBank entry AAA42271 (http://www.ncbi.nlm.nih.gov/protein/554527; accession date Jul. 28, 2009).

Gen Bank entry AAA42268 (http://www.ncbi.nlm.nih.gov/protein/207443; accession date Jul. 28, 2009).

Gen Bank entry AAA42269 (http://www.ncbi.nlm.nih.gov/protein/207445; accession date Jul. 28, 2009).

Gen Bank entry AAA80155 (http://www.ncbi.nlm.nih.gov/protein/473274; accession date Jul. 28, 2009).

GenBank entry AAA49082 (http://www.ncbi.nlm.nih.gov/protein/212742; accession date Jul. 28, 2009).

GenBank entry P04985 (http://www.ncbi.nlm.nih.gov/protein/119293; accession date Jul. 28, 2009).

GenBank entry ABF82224 (http://www.ncbi.nlm.nih.gov/protein/106635760; accession date Jul. 28, 2009).

GenBank entry ABF82222 (http://www.ncbi.nlm.nih.gov/protein/106635720; accession date Jul. 28, 2009).

GenBank entry P11547 (http://www.ncbi.nlm.nih.gov/protein/119298; accession date Jul. 28, 2009).

International Report on Patentability for PCT/AU2007/001738.

* cited by examiner

SEQUENCE LISTING

```
<160> NUMBER OF SEQ ID NOS: 26

<210> SEQ ID NO 1
<211> LENGTH: 9
<212> TYPE: PRT
<213> ORGANISM: Homo sapiens

<400> SEQUENCE: 1

Ala Ala Ala Lys Ala Ala Lys Ala Ala
1               5

<210> SEQ ID NO 2
<211> LENGTH: 5
<212> TYPE: PRT
<213> ORGANISM: Homo sapiens

<400> SEQUENCE: 2

Gly Val Gly Val Pro
1               5

<210> SEQ ID NO 3
<211> LENGTH: 4
<212> TYPE: PRT
<213> ORGANISM: Homo sapiens

<400> SEQUENCE: 3

Gly Gly Val Pro
1

<210> SEQ ID NO 4
<211> LENGTH: 6
<212> TYPE: PRT
<213> ORGANISM: Homo sapiens

<400> SEQUENCE: 4

Gly Val Gly Val Ala Pro
1               5

<210> SEQ ID NO 5
<211> LENGTH: 18
<212> TYPE: PRT
<213> ORGANISM: Homo sapiens

<400> SEQUENCE: 5

Gly Gly Val Pro Gly Ala Ile Pro Gly Gly Val Pro Gly Gly Val Phe
1               5                   10                  15

Tyr Pro

<210> SEQ ID NO 6
<211> LENGTH: 9
<212> TYPE: PRT
<213> ORGANISM: Homo sapiens

<400> SEQUENCE: 6

Gly Val Gly Leu Pro Gly Val Tyr Pro
```

```
1               5

<210> SEQ ID NO 7
<211> LENGTH: 7
<212> TYPE: PRT
<213> ORGANISM: Homo sapiens

<400> SEQUENCE: 7

Gly Val Pro Leu Gly Tyr Pro
1               5

<210> SEQ ID NO 8
<211> LENGTH: 13
<212> TYPE: PRT
<213> ORGANISM: Homo sapiens

<400> SEQUENCE: 8

Pro Tyr Thr Thr Gly Lys Leu Pro Tyr Gly Tyr Gly Pro
1               5                   10

<210> SEQ ID NO 9
<211> LENGTH: 13
<212> TYPE: PRT
<213> ORGANISM: Homo sapiens

<400> SEQUENCE: 9

Gly Gly Val Ala Gly Ala Ala Gly Lys Ala Gly Tyr Pro
1               5                   10

<210> SEQ ID NO 10
<211> LENGTH: 10
<212> TYPE: PRT
<213> ORGANISM: Homo sapiens

<400> SEQUENCE: 10

Thr Tyr Gly Val Gly Ala Gly Gly Phe Pro
1               5                   10

<210> SEQ ID NO 11
<211> LENGTH: 5
<212> TYPE: PRT
<213> ORGANISM: Homo sapiens

<400> SEQUENCE: 11

Lys Pro Leu Lys Pro
1               5

<210> SEQ ID NO 12
<211> LENGTH: 12
<212> TYPE: PRT
<213> ORGANISM: Homo sapiens

<400> SEQUENCE: 12

Ala Asp Ala Ala Ala Tyr Lys Ala Ala Lys Ala
1               5                   10

<210> SEQ ID NO 13
<211> LENGTH: 9
<212> TYPE: PRT
<213> ORGANISM: Homo sapiens

<400> SEQUENCE: 13

Gly Ala Gly Val Lys Pro Gly Lys Val
1               5
```

```
<210> SEQ ID NO 14
<211> LENGTH: 9
<212> TYPE: PRT
<213> ORGANISM: Homo sapiens

<400> SEQUENCE: 14

Gly Ala Gly Val Lys Pro Gly Lys Val
1               5

<210> SEQ ID NO 15
<211> LENGTH: 9
<212> TYPE: PRT
<213> ORGANISM: Homo sapiens

<400> SEQUENCE: 15

Thr Gly Ala Gly Val Lys Pro Lys Ala
1               5

<210> SEQ ID NO 16
<211> LENGTH: 7
<212> TYPE: PRT
<213> ORGANISM: Homo sapiens

<400> SEQUENCE: 16

Gln Ile Lys Ala Pro Lys Leu
1               5

<210> SEQ ID NO 17
<211> LENGTH: 12
<212> TYPE: PRT
<213> ORGANISM: Homo sapiens

<400> SEQUENCE: 17

Ala Ala Ala Ala Ala Ala Ala Lys Ala Ala Ala Lys
1               5                   10

<210> SEQ ID NO 18
<211> LENGTH: 22
<212> TYPE: PRT
<213> ORGANISM: Homo sapiens

<400> SEQUENCE: 18

Ala Ala Ala Ala Ala Ala Ala Ala Ala Ala Lys Ala Ala Lys Tyr Gly
1               5                   10                  15

Ala Ala Ala Gly Leu Val
            20

<210> SEQ ID NO 19
<211> LENGTH: 16
<212> TYPE: PRT
<213> ORGANISM: Homo sapiens

<400> SEQUENCE: 19

Glu Ala Ala Ala Lys Ala Ala Ala Lys Ala Ala Lys Tyr Gly Ala Arg
1               5                   10                  15

<210> SEQ ID NO 20
<211> LENGTH: 17
<212> TYPE: PRT
<213> ORGANISM: Homo sapiens

<400> SEQUENCE: 20

Glu Ala Gln Ala Ala Ala Ala Lys Ala Ala Lys Tyr Gly Val Gly
1               5                   10                  15

Thr
```

```
<210> SEQ ID NO 21
<211> LENGTH: 17
<212> TYPE: PRT
<213> ORGANISM: Homo sapiens

<400> SEQUENCE: 21

Ala Ala Ala Ala Ala Lys Ala Ala Lys Ala Ala Gln Phe Gly Leu
1               5                   10                  15

Val

<210> SEQ ID NO 22
<211> LENGTH: 29
<212> TYPE: PRT
<213> ORGANISM: Homo sapiens

<400> SEQUENCE: 22

Gly Gly Val Ala Ala Ala Ala Lys Ser Ala Lys Val Ala Ala Lys
1               5                   10                  15

Ala Gln Leu Arg Ala Ala Ala Gly Leu Gly Ala Gly Ile
            20                  25

<210> SEQ ID NO 23
<211> LENGTH: 15
<212> TYPE: PRT
<213> ORGANISM: Homo sapiens

<400> SEQUENCE: 23

Gly Ala Leu Ala Ala Ala Lys Ala Ala Lys Tyr Gly Ala Ala Val
1               5                   10                  15

<210> SEQ ID NO 24
<211> LENGTH: 14
<212> TYPE: PRT
<213> ORGANISM: Homo sapiens

<400> SEQUENCE: 24

Ala Ala Ala Ala Ala Ala Ala Lys Ala Ala Ala Lys Ala Ala
1               5                   10

<210> SEQ ID NO 25
<211> LENGTH: 12
<212> TYPE: PRT
<213> ORGANISM: Homo sapiens

<400> SEQUENCE: 25

Ala Ala Ala Ala Lys Ala Ala Lys Tyr Gly Ala Ala
1               5                   10

<210> SEQ ID NO 26
<211> LENGTH: 11
<212> TYPE: PRT
<213> ORGANISM: Homo sapiens

<400> SEQUENCE: 26

Cys Leu Gly Lys Ala Cys Gly Arg Lys Arg Lys
1               5                   10
```

USE OF TROPOELASTIN FOR REPAIR OR RESTORATION OF TISSUE

FIELD OF THE INVENTION

The present invention relates to tropoelastin and to tissue repair and restoration using elastic materials.

BACKGROUND OF THE INVENTION

Elastin is an extracellular matrix protein that is primarily found in skin, blood vessels, lung and other tissues and organs that require a degree of elasticity for function. It is formed when lysine residues on tropoelastin molecules become cross-linked with lysine residues on other tropoelastin molecules by lysyl oxidase.

Elastin is expected to be useful in medical applications including tissue repair and restoration and in providing biocompatible surfaces for medical devices having pre-determined elasticity. In these applications, elastin is generally made by cross-linking the side chains of lysine residues on recombinant tropoelastin molecules using reagents that react with lysine and other charged residues such as glutaraldehyde.

One problem with elastin produced from recombinant tropoelastin is that the cross-linking agents such as glutaraldehyde may be toxic or otherwise cause unwanted tissue reactions or allergy in some individuals. Further, as the elastic properties of elastin tend to be dependent on cross-linking of lysine side chains, there is a limit to the range of elastic properties that elastin can provide. Also, the requirement for cross-linking precludes the effective delivery via some standard administration routes, for example, injection, because without special precaution, the cross-linking agent may cause the elastin to form prior to delivery to the site at which elastin formation is intended.

There is a need for elastic materials that can be formed without use of a cross-linking agent.

There is also a need for compositions that can be administered to tissue by injection to form an elastic material at a site in connection with the site of injection.

There is also a need for elastic materials having elastic qualities not found in elastin or other proteins and bio-materials used for tissue repair, bulking and wound healing.

There is also a need for new formulations for sustained or controlled release of pharmaceutical compounds and tissue factors and for new cell and tissue matrices.

SUMMARY OF THE INVENTION

The invention seeks to at least minimise one of the above limitations or problems and in certain embodiments provides a process for producing an elastic material from tropoelastin. The process includes the step of heating a solution of tropoelastin having an alkaline pH to form an elastic material from the tropoelastin in the solution.

In other embodiments there is provided a process for producing an elastic material from tropoelastin. The process includes heating a solution of tropoelastin having an alkaline pH of at least about 7.5 and a salt concentration of at least about 25 mM to form an elastic material from the tropoelastin in the solution.

In other embodiments there is provided a process for producing an elastic material from tropoelastin. The process includes providing an alkaline pH to a solution of tropoelastin having a temperature of about 37° C. to form an elastic material from the tropoelastin in the solution.

In other embodiments there is provided a process for producing an elastic material from tropoelastin. The process includes providing an alkaline pH to a solution of tropoelastin and allowing the temperature of the solution to increase to about 37° C. to form an elastic material from the tropoelastin in the solution.

In other embodiments there is provided a process for producing an elastic material from tropoelastin. The process includes adding tropoelastin to a solution having an alkaline pH and a temperature of about 37° C. to form an elastic material from the tropoelastin in the solution.

In other embodiments there is provided a process for producing an elastic material from tropoelastin. The process includes adding tropoelastin to a solution having an alkaline pH and allowing the temperature of the solution to increase to about 37° C. to form an elastic material from the tropoelastin in the solution.

In other embodiments there is provided a process for producing an elastic material from tropoelastin. The process includes adjusting the salt concentration of a solution of tropoelastin having an alkaline pH and a temperature of about 37° C. to form an elastic material from the tropoelastin in the solution.

In other embodiments there is provided a process for producing an elastic material from tropoelastin. The process includes adjusting the salt concentration of a solution of tropoelastin having an alkaline pH and allowing the temperature of the solution to increase to about 37° C. to form an elastic material from the tropoelastin in the solution.

In another embodiment there is provided a bulking agent for bulking a tissue or correcting a tissue defect, the bulking agent being formed from an elastic material produced by a process described above.

In another embodiment there is provided a sealant for a wound, the sealant being formed from an elastic material produced by a process described above.

In another embodiment there is provided a prosthesis or medical device having an elastic material being produced by a process described above.

In another embodiment there is provided a kit for forming an elastic material including a first container including tropoelastin, a second container including a reagent to be added to the tropoelastin to form an alkaline solution including the tropoelastin and written instructions for forming an elastic material from the tropoelastin and the reagent.

In another embodiment there is provided a composition for forming an elastic material including a solution of tropoelastin having an alkaline pH and a temperature selected to prevent the formation of an elastic material from tropoelastin in the solution.

In another embodiment there is provided an apparatus for forming an elastic material from tropoelastin including a first chamber including a solution of tropoelastin; a second chamber including a reagent for adjusting the pH of the solution of the first chamber; dispensing means in use for dispensing the solution of the first chamber and the reagent to form an admixture of the solution and the reagent, to form the elastic material from tropoelastin in the admixture.

In another embodiment there is provided an apparatus for forming an elastic material from tropoelastin including a first chamber including a solution of tropoelastin having an alkaline pH; a second chamber including a solution for providing a salt concentration of about 150 mM or less to the solution of the first chamber; and dispensing means in use for dispensing the solutions of the first chamber and second chambers to form an admixture of the solutions, to form the elastic material from tropoelastin in the admixture.

In another embodiment there is provided a sustained or controlled release implant the implant being formed from an elastic material produced by a process described above.

In another embodiment there is provided a cell or tissue matrix, the cell or tissue matrix being formed from an elastic material produced by a process described above.

In another embodiment there is provided a method of forming a purified solution of tropoelastin including:
  providing a solution of tropoelastin;
  adjusting the pH of the solution to form a solution having alkaline pH, to cause the tropoelastin in the solution to precipitate;
  removing the precipitate;
  adding the removed precipitate to a solution having a substantially non alkaline pH, and/or a substantially lowered temperature, to cause the precipitate to disperse into the solution, to form a purified solution of tropoelastin.

In another embodiment there is provided a method of forming an elastic material from solution of tropoelastin including:
  (1) providing a solution of tropoelastin;
  (2) adjusting the pH of the solution to form a solution having alkaline pH, to cause the tropoelastin in the solution to precipitate;
  (3) removing the precipitate;
  (4) adding the removed precipitate to a solution having a substantially non alkaline pH, and/or a substantially lowered temperature, to cause the precipitate to disperse into the solution; and
  (5) allowing the temperature of the solution to increase to about 37° C. to form an elastic material from the tropoelastin in the solution.

DETAILED DESCRIPTION OF THE EMBODIMENTS

Figure 1:
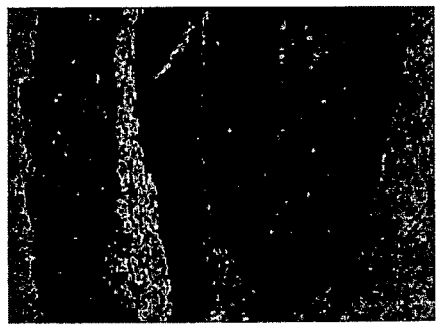
FIG. 1: H&E stained slice collected from rat injection site 15 days post injection.

The inventors have found that a solution of tropoelastin can be made to form an elastic material by adjusting the alkalinity, temperature or salt concentration of the solution. In certain embodiments, the elastic material is formed by adjusting temperature and/or alkalinity only. In other certain embodiments, the elastic material may have a salt concentration of 0 mM.

The elastic material that the inventors have developed is not the same as elastin because it does not require cross-linking of tropoelastin molecules for its formation. In contrast, elastin is formed when tropoelastin is cross-linked by lysyl oxidase or glutaraldehyde or like agents.

One advantage is that the elastic material of the invention is generally more bio-compatible because it does not contain chemical cross-linkers. It will be understood, however, that the elastic material of the invention may be cross-linked with lysyl oxidase or other chemical agents such as glutaraldehyde.

Another advantage is that the elastic material of this invention may be provided with properties that cannot be found in elastin. These properties include the tensile and extensile strength, recoil, compressibility, biodegradability and persistence, particularly in a tissue or body cavity. Accordingly, with the invention, tropoelastin can be used to provide devices, prostheses and tissue repair agents that have not been obtainable using elastin.

A further advantage is that the formation of the elastic material can be controlled simply by adjusting temperature, pH or salt. As demonstrated herein, this permits one to more effectively form an elastic material in a tissue by an administration route such as injection.

It will be understood that an "elastic material" refers to a material that can be formed from tropoelastin without cross-linking amino acid residues of tropoelastin that are otherwise cross-linked when elastin is naturally formed (for example by lysyl oxidase) or when elastin is manufactured (for example by glutaraldehyde). Once formed, the elastic material of the invention may be cross-linked with lysyl oxidase or other chemical agents such as glutaraldehyde.

As discussed below an "elastic material" may also include other components.

Generally an "elastic material" is not a free-flowing liquid. It may be a gel, paste, solid, or other phase that significantly lacks the properties of flow. Advantageously, according to the invention, one can design or otherwise select the properties of the phase that is required by manipulating parameters of temperature, pH or salt during formation of the elastic material, or otherwise by cross-linking the material with an agent capable of cross-linking the cross-linkable amino acid side chains, where an example of such a cross-linker is glutaraldehyde.

An "elastic material" generally returns to a particular shape or conformation after a force such as compression or extension that has been applied to it has been withdrawn.

"Elastic material" is also referred to as a resiliently compressible and extendible, mechanically durable, or pliable material of relatively low hysteresis. This material may be referred to as stretchable, tensile, resilient or capable of recoil.

It is possible to visually observe the formation of an elastic material from a solution of tropoelastin. The solution of tropoelastin is substantially clear. As the elastic material forms, the solution decreases in clarity and becomes opaque due to a transitional precipitate-like phase. The elastic material is substantially in solid form as mentioned above and may have various appearances depending on its composition. The formation of the elastic material may also be observed using any appropriate analytical technique known in the art, such as monitoring for a change in temperature or transmission.

It will be understood that "tropoelastin" generally means a peptide that includes or consists of a sequence that is the same as or similar to a hydrophilic domain of tropoelastin. A hydrophilic domain has a sequence that is typically rich in lysine and alanine residues. These domains often consist of stretches of lysine separated by 2 or 3 alanine residues such as AAA-KAAKM (SEQ ID NO: 1). Other hydrophilic domains do not contain the poly-alanine tract, but have lysine near a proline instead. In contrast, tropoelastin hydrophobic domains are rich in non-polar amino acids especially glycine, valine, proline and alanine and often occur in repeats of 3 to 6 peptides such as GVGVP (SEQ ID NO: 2), GGVP (SEQ ID NO: 3) and GVGVAP (SEQ ID NO: 4).

It is important that the peptide that is used to form the elastic material includes at least part of the hydrophilic domain as this domain is believed to be important for causing the elastic material to form when alkalinity, temperature or salt concentration of the tropoelastin solution is adjusted.

Examples of tropoelastin that could be used to form the elastic material of the invention are those that consist of a hydrophilic domain or a homolog thereof, and those that include a hydrophilic domain or homolog and part or all of a hydrophobic domain. Some examples are set out below:

| | |
|---|---|
| GGVPGAIPGGVPGGVFYP, | (SEQ ID NO: 5) |
| GVGLPGVYP, | (SEQ ID NO: 6) |
| GVPLGYP, | (SEQ ID NO: 7) |
| PYTTGKLPYGYGP, | (SEQ ID NO: 8) |
| GGVAGAAGKAGYP, | (SEQ ID NO: 9) |
| TYGVGAGGFP; | (SEQ ID NO: 10) |
| KPLKP, | (SEQ ID NO: 11) |
| ADAAAAYKAAKA, | (SEQ ID NO: 12) |
| GAGVKPGKV, | (SEQ ID NO: 13) |
| GAGVKPGKV, | (SEQ ID NO: 14) |
| TGAGVKPKA, | (SEQ ID NO: 15) |
| QIKAPKL, | (SEQ ID NO: 16) |
| AAAAAAAKAAAK, | (SEQ ID NO: 17) |
| AAAAAAAAAAKAAKYGAAAGLV, | (SEQ ID NO: 18) |
| EAAAKAAAKAAKYGAR, | (SEQ ID NO: 19) |
| EAQAAAAAKAAKYGVGT, | (SEQ ID NO: 20) |
| AAAAAKAAAKAAQFGLV, | (SEQ ID NO: 21) |
| GGVAAAAKSAAKVAAKAQLRAAAGLGAGI, | (SEQ ID NO: 22) |
| GALAAAKAAKYGAAV, | (SEQ ID NO: 23) |
| AAAAAAAKAAAKAA, | (SEQ ID NO: 24) |
| AAAAKAAKYGAA, | (SEQ ID NO: 25) |
| CLGKACGRKRK. | (SEQ ID NO: 26) |

"Tropoelastin" may have a sequence that is the same as the entry shown in GenBank entry AAC98394. Other tropoelastin sequences including a hydrophilic domain are known in the art, including, but not limited to, CAA33627 (*Homo sapiens*), P15502 (*Homo sapiens*), AM42271 (*Rattus norvegicus*), AAA42272 (*Rattus norvegicus*), AAA42268 (*Rattus norvegicus*), AAA42269 (*Rattus norvegicus*), AAA80155 (*Mus musculus*), AAA49082 (*Gallus gallus*), P04985 (*Bos taurus*), ABF82224 (*Danio rerio*), ABF82222 (*Xenopus tropicalis*), P11547 (*Ovis aries*).

"Tropoelastin" may also be a fragment of these sequences provided that the fragment includes at least part of a hydrophilic domain as discussed above. An example is amino acids 27 to 724 of AAC98394.

Tropoelastin may also include a homolog of a peptide having a sequence such as described above, in particular AAC98394, or be a homolog of a peptide having a sequence such as described above, or be a fragment of a homolog of a peptide having a sequence such as described above. Herein "homolog" refers to a protein having a sequence that is not the same as, but that is similar to, a reference sequence. It also has the same function as the reference sequence, for example, a capacity to form an elastic material when a solution of the homolog is manipulated to adjust alkalinity, temperature or salt concentration as discussed herein.

In certain embodiments the homolog has at least 60% homology to a peptide such as described above, in particular AAC98394 or a fragment of a peptide such as described above that includes at least part of a hydrophilic domain.

It will be understood that "tropoelastin" may be natural or recombinant.

Herein "elastin-like peptides" (ELP) refers to compounds formed by the polymerizing of small amino acid sequences (typically less than 5 amino acids in length) isolated from the hydrophobic regions of tropoelastin or elastin that are essential for coacervation of the molecules. Some commonly used sequences include GVGVP (SEQ ID NO: 2), GGVP (SEQ ID NO: 3), and GVGVAP (SEQ ID NO: 4).

The inventors have found that there exists a subset of temperature, alkalinity, and salt concentration conditions within which a solution of tropoelastin can be made to form an elastic material. While not wanting to be bound by hypothesis, it is believed that these conditions influence an interaction between hydrophilic domains of tropoelastin molecules that leads to formation of the elastic material. Hence the elastic material is not the same as natural or artificial elastin that is formed by cross-linking of charged amino acid side chains. Nor is it the same as the material that is formed by coacervation of ELP.

Thus in one embodiment there is provided a process for producing an elastic material from tropoelastin including heating a solution of tropoelastin having an alkaline pH to form an elastic material from the tropoelastin in the solution.

In other embodiments there is provided a process for producing an elastic material from tropoelastin including providing an alkaline pH to a solution of tropoelastin having a temperature of about 37° C. to form an elastic material from the tropoelastin in the solution.

In other embodiments there is provided a process for producing an elastic material from tropoelastin including providing an alkaline pH to a solution of tropoelastin and allowing the temperature of the solution to increase to about 37° C. to form an elastic material from the tropoelastin in the solution.

In other embodiments there is provided a process for producing an elastic material from tropoelastin including adding tropoelastin to a solution having an alkaline pH and a temperature of about 37° C. to form an elastic material from the tropoelastin in the solution.

In other embodiments there is provided a process for producing an elastic material from tropoelastin including adding tropoelastin to a solution having an alkaline pH and allowing the temperature of the solution to increase to about 37° C. to form an elastic material from the tropoelastin in the solution.

In other embodiments there is provided a process for producing an elastic material from tropoelastin including adjusting the salt concentration of a solution of tropoelastin having an alkaline pH and a temperature of about 37° C. to form an elastic material from the tropoelastin in the solution.

Generally a solution of tropoelastin concentration greater than about 1.5 mg/mL is capable of forming an elastic material of desirable integrity although lesser concentrations are also useful. In most applications the solution concentration is less than about 300 mg/mL. Therefore, a solution of tropoelastin having a concentration from about 1.5 mg/mL to about 300 mg/mL is preferable. More preferably, a solution of tropoelastin having a concentration between about 10 mg/mL to about 300 mg/mL is used. Most preferably, a solution of tropoelastin having a concentration of between about 10 mg/mL to about 200 mg/mL is used.

It has been determined that a pH of about pH 7.5 or more is sufficient to cause an elastic material to form from the tropoelastin in the solution. The pH is generally kept from exceeding about pH 13 as above this the elastic material is less well formed. More preferably a pH of between about pH 9 and pH 13 is desirable. However, most preferably a pH of between about pH 10 and pH 11 is used. Other pH measures that could be used include 8.0, 8.5, 9.5, 10, 10.5, and 11.5.

Alkalinity can be adjusted by a number of approaches including 1) directly adding a pH increasing substance to a solution of tropoelastin, 2) by mixing a solution containing sufficient amounts of a pH increasing substance to cause it to be alkaline with a solution of tropoelastin. The pH increasing substance could be a base, buffer, proton adsorbent material. Examples including Tris base, $NH_4OH$ and NaOH have been found to be useful as pH increasing or controlling substances.

Where the pH is alkaline and less than about 9.5, salt may be required to form the elastic material of the invention. Where salt is used, the concentration is generally more than 25 mM and may be up to 200 mM. Preferably, the salt concentration is between about 100 mM and 150 mM. More preferably, the salt concentration is about 150 mM. In particular, the inventors have found that as pH decreases (and yet remains alkaline) below pH 10, salt is required to cause formation of the elastic material and the amount of salt required increases as pH decreases. So for example, at about pH 9 to 10, salt is required, for example a salt concentration equivalent to about 60 mM should be provided to the solution. In some embodiments, the solution is to have an osmolarity equivalent to that of mammalian isotonic saline (150 mM) or less. In other embodiments, the solution is to have an osmolarity greater than 150 mM. The salt concentration may also be 0 mM.

The salt concentration of the solution may be controlled by adding salt, including any ionic compound, monovalent or divalent ions, or low molecular weight species capable of affecting the osmolality of the solution. For instance, NaCl, KCl, $MgSO_4$, $Na_2CO_3$ or glucose may be used. A preferred salt is NaCl.

In another embodiment there is provided a method of forming an elastic material from solution of tropoelastin including:
(1) providing a solution of tropoelastin;
(2) adjusting the pH of the solution to form a solution having alkaline pH, to cause the tropoelastin in the solution to precipitate;
(3) removing the precipitate;
(4) adding the removed precipitate to a solution having a substantially non alkaline pH, and/or a substantially lowered temperature, to cause the precipitate to disperse into the solution; and
(5) allowing the temperature of the solution to increase to about 37° C. to form an elastic material from the tropoelastin in the solution.

In one embodiment the temperature of the solution is preferably between about 4° C. to about 37° C. at step (2) and less than about 4° C. at step (4). Further, in one embodiment the pH of the solution is preferably at least about pH 9 at step (2) and less than about pH 9 at step (4). The pH may be as low as about pH 7.5 at step (4). Further still, in one embodiment the salt concentration of the solution is preferably between about 0 mM and 200 mM.

Thus, in other embodiments there is provided a process for producing an elastic material from tropoelastin including heating a solution of tropoelastin having an alkaline pH that is less than 10 and a salt concentration of 150 mM or less to form an elastic material from the tropoelastin in the solution. These embodiments are particularly preferable for in vivo applications since the pH of the solution of tropoelastin and the elastic material is closer to mammalian pH.

In further embodiments there is provided a process for producing an elastic material from tropoelastin including adjusting the salt concentration of a solution of tropoelastin having an alkaline pH and allowing the temperature of the solution to increase to about 37° C. to form an elastic material from the tropoelastin in the solution.

It has been determined that a temperature of around 37° C. is preferable to cause an elastic material to form from the tropoelastin in the solution. However, in certain embodiments a temperature of less than 37° C. may be used. Generally the temperature is greater than 4° C. It is generally less than 42° C. The inventors have found that the temperature required to form an elastic material is inversely related to the concentration of tropoelastin in the solution of tropoelastin. That is, a solution with a low concentration of tropoelastin will require a higher temperature to form an elastic material. The inventors have also found that the pliability increases, and the integrity persists longer, as a function of the time the tropoelastin solution is held at a certain temperature.

The solution may be heated by providing the solution in or on a mammalian tissue and allowing the heat transfer from the tissue to increase the temperature of the solution, or by irradiating the tissue.

Alternatively, the solution may be heated by contacting the solution with an inanimate surface and heating the surface. The inanimate surface may be provided on a mold or cast for providing the elastic material formed by the method with a pre-defined shape or conformation, and may further be provided on a prosthesis, stent or like device.

Where heating of the solution is provided to trigger the formation of the elastic material (i.e. where appropriate pH and/or salt conditions have been provided), the solution is generally stored at temperatures below 30° C., preferably about 4° C., until it is required for forming an elastic material.

It is preferable that the majority of tropoelastin initially in solution be used to form the elastic material.

In certain embodiments the elastic material formed from a solution of tropoelastin by a process described above may be cross-linked with an agent capable of cross-linking the side chains of residues of tropoelastin such as lysine. As discussed herein, cross-linking is not necessary for the formation of the elastic material and indeed this is a point of distinction between the elastic material of the invention and elastin. While not wishing to be bound by theory, the inventors believe the elastic material forms at least in part due to a combination of charge interactions including charged tyrosine, lysine and arginine residues, as well as stabilizing hydrogen bonds. The inventors believe that dityrosine may be formed. Importantly, these interactions occur in the absence of a cross-linking agent.

However, in certain applications described below, it is useful to cross-link these side chains when the elastic material has been formed as this provides further properties to the elastic material. Specifically, in comparison to the elastic material formed in the absence of cross-linker, the use of a cross-linker such as glutaraldehyde gives an elastic material that is stiffer, denser, tougher, and therefore likely more biostable in vivo. The inventors suggest that this material may be preferable over the non-cross-linked elastic material for more demanding tissue restoration applications or when compliance with the surrounding natural tissue is non-essential. Of note, when glutaraldehyde is added to an alkaline pH solution of tropoelastin, the inventors have surprisingly found that a distinctive colour appears as the elastic material forms, which may be clinically useful as a determinant of solid formation.

It is contemplated that any cross-linking agent that can be used to form elastin, whether naturally or artificially, may be used. Examples include lysyl oxidase, transglutaminase, glutaraldehyde, genipin and amine-reactive cross-linkers such as BS3. In one embodiment, the cross-linking agent is glutaraldehyde and is used at a concentration of about 0.001 w/v % solution to about 0.5 w/v % solution.

The process of the invention and the elastic material formed from this are particularly useful in tissue bulking applications, for example, applications where there is a need to cosmetically enhance or improve appearance (for example, plumping of lips, filling-in of nasolabial folds, reduction of wrinkles or other tissue enhancements), or medical applications where there is a need to support a congenital defect, or defect caused by disease or surgical resection.

In more detail, as the formation of the elastic material can be controlled simply by adjusting temperature, pH or salt, this permits one to form a bulking agent in situ by injecting a tropoelastin solution having, or having had, an alkaline pH into a desired site and allowing heat transfer from the tissue to cause the elastic material to form. Further, the timing of the formation of the elastic material, and the elastic properties and persistence of the material so formed can be adjusted by manipulating salt or pH, or by adding cross-linking agents after the elastic material has formed.

A major benefit is that the bulking agent can effectively be provided by using a fine gauge needle. In this mode of administration, the viscosity of the tropoelastin solution for forming the bulking agent can be controlled by manipulating one or more of temperature, pH or salt concentration, or the incubation time at high pH prior to lowering the pH in preparation for injection.

The tropoelastin solution can be injected either intra-dermally or subcutaneously, or deeper in or below the dermis, or into other tissue, in order to provide a depot of elastic material.

Accordingly, in one embodiment the invention provides a method for cosmetically enhancing a tissue including injecting a solution containing tropoelastin into a tissue requiring cosmetic enhancement to form an elastic material according to a process described above in the tissue. The cosmetic enhancement may be to remove or reduce skin wrinkles, to plump lips or otherwise to reduce or re-shape the appearance of a tissue, tissue profile, or facial feature. The tropoelastin solution may be kept cool for example about 4° C. before injection and warmed to body temperature by heat transfer from the tissue. Alternatively, an external energy source may be used to irradiate the tissue to increase the temperature of the tropoelastin solution to form the elastic material in the tissue.

The tropoelastin solution can also be applied to the surface of a tissue to provide a coverage or support by the elastic material.

Accordingly, in another embodiment, the invention provides a method for supporting a tissue or organ at a site of disease, trauma, surgical resection or other wound including injecting or otherwise applying a solution containing tropoelastin in or about a tissue or organ requiring support to form an elastic material according to a process described above in or about the tissue or organ. In one example the solution of tropoelastin is injected to form an elastic material that provides augmentation about the site of a sphincter, such as would be required for bulking around the bladder sphincter as a form of treatment of urinary incontinence.

In the above embodiments, the alkaline tropoelastin solution may be cooled, for example to about 4° C., before injection and then warmed to body temperature by heat transfer from the tissue. Alternatively, an external energy source may be used to irradiate the tissue to increase the temperature of the tropoelastin solution to form the elastic material in the tissue.

It will be understood that the elastic material may be prepared externally according to a process described above and then inserted into a tissue or tissue cavity.

For example, the tropoelastin solution may be cast into a mold and elastic material formed according to a process described above in order to generate an appropriate shape for subsequent implantation into a patient. An example is where surgical removal of part of a patient's tissue leaves a cavity requiring filling with a biocompatible elastic material. Under these conditions, the shape of the location that requires filling may be assessed using known methods and an appropriate mold prepared based on this assessment. The tropoelastin solution is then cast within the mold and an elastic material formed according to a process described above for implantation within the location requiring filling.

In another example, the tropoelastin solution may be formed into an elastic material according to a process described above in the form of particles. For instance, the particles may be formed using an emulsion, microfluidic, or other system as known in the art for making particles. The particles may also be formed from a tropoelastin solution of tropoelastin concentration lower than about 1.5 mg/mL. The particles may be substantially spherical and have a diameter ranging from 0.1 micrometers to 10 micrometers. The particles of elastic material can be delivered to the location requiring treatment using high velocity delivery techniques known in the art.

One advantage of forming the elastic material from a tropoelastin solution according to a process described above is that the elastic material can be made to form rapidly, indeed more quickly than can be achieved when elastin is formed. This enables a variety of intricate and complex shapes to be formed in a mold that cannot be formed by elastin. A further advantage is that as the rate of formation of the elastic material from a tropoelastin material can be controlled by manipulating temperature, pH and/or salt, gases can be introduced in a controlled process to form bubbles and generate an open sponge-like matrix. Alternatively, formation of bubbles can be avoided if desired.

Another approach to forming a tissue implant externally is the use of techniques including laser based lithography, electrospraying and electrospinning.

The elastic material formed from a tropoelastin solution according to a process described above is particularly useful for sealing wounds, or for adding support to newly repaired wounds, in particular wounds where granulation tissue has been laid down but substantial fibrosis that would otherwise give strength to the healed wound has not occurred. Examples of these wounds include surgical wounds, or wounds caused by trauma, such as laceration, abrasion, puncture, or burns or other defects. The wounds may be located dermally, subcutaneously, in deep tissue or in an organ requiring at least some elasticity for function.

The elastic material formed from the solution of tropoelastin according to a process described above is useful in circumstances in which fibrin sealants and surgical glues are conventionally used. One example is where an anastomosis requires effective sealing to reduce fluid loss. Another example is where there is a need to rapidly stem blood flow, or to prevent invasion by micro-organisms.

There are a number of routes of administration. These include spraying, wiping, pouring, pasting or contacting a tropoelastin solution onto the wound to cause the elastic material to form according to a process described above, in and/or on the surface of the wound.

Thus in one embodiment there is provided a method for sealing a tissue wound including spraying, pasting, pouring, wiping or contacting a solution of tropoelastin against a tissue wound to cause an elastic material to form according to a process described above.

In these embodiments, the solution of tropoelastin can be supplemented with other compounds, proteins and factors to facilitate, modulate or enhance sealing of a wound.

As noted above, one advantage of forming the elastic material from a tropoelastin solution according to a process described above is that the elastic material can be made to form rapidly, indeed more quickly than can be achieved when elastin is formed. Accordingly, it is envisaged that it would be possible to obtain rapid sealing of a wound. Further, the fact that manipulation of temperature, pH and/or salt affects the rate of formation of the elastic material means that the rate of sealing of a wound can be controlled more effectively.

Further to the tissue support and bulking agents described above, the elastic material formed from a tropoelastin solution according to a process described above is particularly useful for the manufacture of prostheses and medical devices. Examples include grafts or stents for holding open biological structures such as vessels and chambers. Other examples include bands for assisting biological structures with recoil.

A further application is to provide a biocompatible coating to an otherwise biologically incompatible medical device (such as a pacemaker or cochlear implant) that is elastic, resilient and capable of persisting at a tissue site. In these embodiments, the elastic material is particularly important for avoiding fibrosis.

The fact that the elastic material can be made to form rapidly, indeed more quickly than can be achieved when elastin is formed, means that a thin evenly surface coating can be applied to a medical device, providing biocompatibility without interfering with performance of the device.

In other embodiments there are provided kits and compositions useful for forming an elastic material using a tropoelastin solution according to a method described above. In one form, a kit includes a first container including tropoelastin, a second container including a reagent for providing an alkaline solution, and written instructions for forming an elastic material using the tropoelastin and the reagent.

In one embodiment there is provided a composition for forming an elastic material including a solution of tropoelastin having an alkaline pH and a temperature selected to prevent the formation of an elastic material from tropoelastin in the solution. The composition may include salt, particularly where the pH of the solution is less than pH 10, as discussed above. In certain forms, the composition may be provided in a powdered form which in use is to be hydrated to provide a solution of tropoelastin. On heating, the elastic material is formed from the tropoelastin in the solution.

Depending on the use to which the kits and compositions are to be put (for example, for tissue bulking, wound sealing or other applications described herein), the kits and compositions may also be provided with further molecules. For example, other connective tissue molecules may be provided in formulation with, or for formulation with, tropoelastin. Examples include collagen, elastin, keratin, fibrin, glycosaminoglycans such as hyaluronan and heparin sulfate, chondroitins and like molecules. Artificial forms of these molecules may also be provided, for examples, ELPs.

In other forms, pharmaceutical compounds, including antibiotics, growth promoters, antiseptics, angiogenic compounds, anti-cancer agents, and the like, may be provided for formulation with, or in formulation with, tropoelastin.

Further forms may provide biological factors such as tissue factors, cytokines, growth factors and the like. Particularly preferred are those factors involved in wound healing, fibrosis and granulation.

Other forms may provide cells, in particular, cells that are involved in wound healing. Examples include epithelial cells, fibrocytes, fibroblasts, keratinocyte precursors, keratinocytes, myofibroblasts, phagocytes and the like.

In another embodiment there is provided an apparatus or device for forming an elastic material from tropoelastin including a first chamber including a solution of tropoelastin; a second chamber including a reagent for adjusting the pH of the solution of the first chamber; dispensing means for dispensing the solution of the first chamber and the reagent of the second chamber to form an admixture of the solution and the reagent, to form the elastic material from tropoelastin in the admixture.

In another embodiment there is provided an apparatus for forming an elastic material from tropoelastin including a first chamber including a solution of tropoelastin having an alkaline pH; a second chamber including a solution for providing a salt concentration of about 150 mM or less to the solution of the first chamber; and dispensing means for dispensing the solutions of the first and second chambers to form an admixture of the solutions, to form the elastic material from tropoelastin in the admixture.

These apparatuses may be used to apply the tropoelastin solution for formation of an elastic product according to a process described above by spraying, pasting, smearing or injecting the solution to a desired tissue site or to an inanimate surface such as a mold. For example, the apparatus may be adapted to be connectable to a fine gauge needle. In another form the apparatus may be adapted to be connectable to an atomiser.

It will be understood that the apparatus may contain other molecules, compounds, factors and cells as described above in the first or second chamber, or in a further chamber of the apparatus.

The inventors have discovered that a precursor or intermediate form of the elastic material of the invention can be generated which may be returned to solution form when the pH, salt concentration, or temperature are appropriately manipulated. In more detail, the inventors have found that when the pH of a tropoelastin containing solution is adjusted to above about pH 9 at temperatures more than about 4° C., preferably about 37° C., a precipitate is formed that can then be separated from solution. When the pH is then lowered to non-alkaline conditions and/or the temperature is lowered, it is possible to cause the precipitate to disassociate and disperse. The dispersed precipitate contains at least some free tropoelastin.

This discovery is expected to be particularly useful in the purification of tropoelastin from recombinant expression systems.

In another embodiment there is provided a method of forming a purified solution of tropoelastin including:
  providing a solution of tropoelastin;
  adjusting the pH of the solution to form a solution having alkaline pH, to cause the tropoelastin in the solution to precipitate;
  removing the precipitate;
  adding the removed precipitate to a solution having a substantially non alkaline pH, and/or a substantially lowered temperature, to cause the precipitate to disperse into the solution, to form a purified solution of tropoelastin.

One particularly important application of the elastic material formed from a tropoelastin solution according to a method described above is to provide a mechanism for sustained or controlled release of a compound. More specifically, by manipulating the pH or salt during formation of the material, or by cross-linking the material with glutaraldehyde or other cross-linking agents after the material is formed, it is possible to design or select an elastic material that has particular persistence qualities. For example, the inventors have found that cross-linked forms of the elastic material tend to be stiffer, denser and more robust than non cross-linked forms. The latter tend to more closely resemble naturally occurring elastin. Some forms tend to be more easily degraded in tissue, hence providing a quicker burst release of a pharmaceutical or like molecule seeded within the elastic material. Other forms are more persistent, less readily degraded and provide a longer term of release of a pharmaceutical or like molecule.

Thus in one embodiment there is provided a sustained or controlled release implant, the implant being an elastic material that is formed from a solution of tropoelastin according to a process described above. The sustained release implant may contain molecules, compounds, factors and cells as described above.

As discussed above, as the rate of formation of the elastic material from a tropoelastin solution can be controlled by manipulating temperature, pH and/or salt, gases may be introduced in a controlled process to form bubbles and generate an elastic material having an open sponge-like matrix. This provides a particularly useful scaffold or matrix for seeding cells, tissues and factors for enabling tissue regeneration and wound repair. Examples of suitable cells and factors are discussed above.

Advantageously, the porosity of the elastic material can be controlled, enabling a structure to be formed through which regenerating tissue can penetrate. Alternatively, a structure can be formed having pores which are sufficient to allow the diffusion of molecules and factors into and out of the elastic material only.

Thus in another embodiment there is provided a cell or tissue matrix, the cell or tissue matrix being formed from an elastic material produced by a process described above.

EXAMPLES

Example 1

Formation of Elastic Material in the Absence of Cross-Linking Agent

Tropoelastin is preferably mixed at a concentration of more than 1.5 mg/mL, typically 10-200 mg/mL in phosphate buffered saline and the solution is adjusted using 1M NaOH to a pH of between about pH 9 to about pH 13, preferably pH 11. The solution is then warmed above 4° C. preferably to about 37° C. A soft paste-like entity is formed which then sets to form the elastic material.

Example 2

Formation of Elastic Material at Lower Alkaline pH Ranges with Salt

Tropoelastin was dissolved in an aqueous solution at a concentration of 10 mg/mL. The salt concentration and pH of the aqueous solution were titrated between 0-150 mM and pH 7-12, respectively. The temperature of the tropoelastin solution was raised to 37° C. and the ability to form an elastic material assessed visually and tactilely. Any elastic material thus formed was tested for its persistence upon cooling.

Two transition points were seen as the pH decreased. Above a pH of 10, there was no need for salt within the solution in order to form a persistent elastic material from the tropoelastin in the solution. However, as the pH decreased below 10, a salt concentration of approximately 60 mM was needed in order to form a persistent elastic material from the tropoelastin in the solution.

Example 3

Elastic Material Formation in Presence of Cross-Linker

A solution of tropoelastin is mixed at a concentration of more than 1.5 mg/mL, typically 10-200 mg/mL with glutaraldehyde (0.001-0.5 % w/v) in phosphate buffered saline at an alkaline pH of approximately 8.5 and warmed to form an elastic material. The material has a pinkish colour and a higher density and stiffness than elastic material formed according to Examples 1 and 2.

Example 4

Purification of Tropoelastin

A crude tropoelastin containing supernatant obtained from a bacterial expression system was adjusted to give a pH between 9 and 13, preferably 11, to precipitate tropoelastin molecules from the solution to form a precipitate. The precipitate was separated from the supernatant and resuspended in a buffer having a non alkaline pH and a lower temperature to cause the precipitate to disperse to form a solution in the buffer. The solution was then stored under refrigeration conditions.

Example 5

Elastic Material Formation In Vivo

A single bolus dose (0.1 ml) of pH adjusted 200 mg/ml tropoelastin solution was injected intradermally using a 26-gauge needle into a healthy female Sprague Dawley rat. The body temperature of the rat led to the rapid onset of heat induced elastic material formation. The animal was observed over a period of 15 days and then examined histologically. A substantial amorphous material was present in the hypodermis including the loose connective tissue beneath the cutaneous muscle (FIG. 1). The presence of a persistent elastic material in this large deposit was confirmed by immunohistostaining with BA4 elastin-specific antibody.

Example 6

Elastic Material with Incorporated Drugs

Elastic material was made by adjusting pH to 10.8, incubating at 37° C. for 1 hr, cooling then readjusting pH to 7.4. Particles of the drug paclitaxel were embedded in the sample. On warming to 37° C. the sample set to give an elastic material that contained distributed particles of the drug. H1299 lung cancer cells were seeded on and around the prepared elastic material. A control elastic material sample contained no paclitaxel. Cells seeded on elastic material containing paclitaxel were observed to be apoptotic. Cells invaded the control samples. Control samples and elastic material that contained paclitaxel but did not contact cells were not apoptotic.

Example 7

Elastic Material and Cell Interaction

Figure 2:
FIG. 2: H&E stained slice of elastic material with embedded fibroblasts. Cells are present in pores within elastic material.
Figure 2:
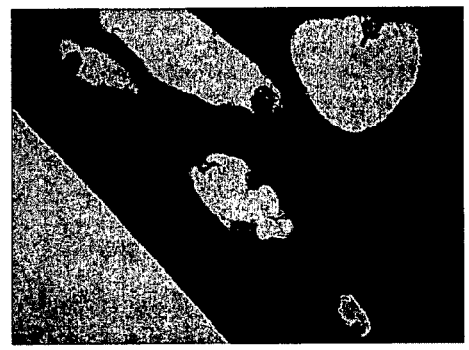
Figure 3:
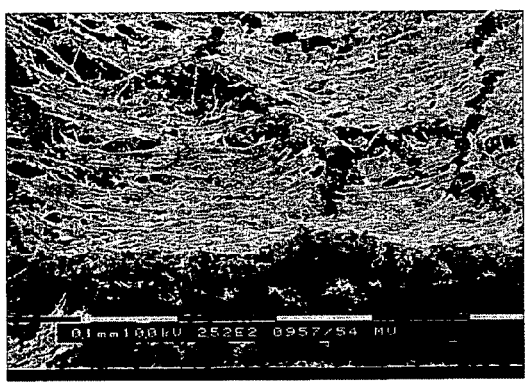
FIG. 3: SEM images showing sheet of fibroblast cells growing on top of elastic material.
Figure 3:
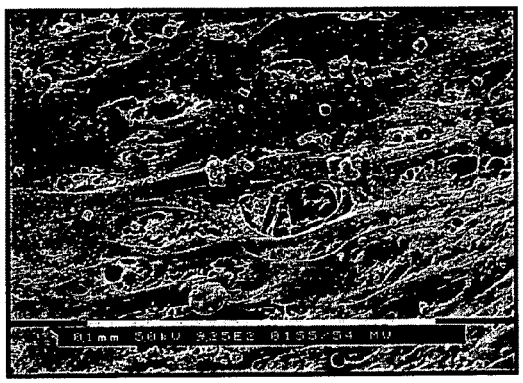

Fibroblast cells were incorporated into (FIG. 2), or seeded on top of (FIG. 3), elastic material.

---

The invention claimed is:

1. A process for producing an elastic material from tropoelastin including:
heating a solution of tropoelastin having an alkaline pH of about 9 or greater;
holding the solution at the heated temperature in the absence of a cross-linking agent for a sufficient period of time to form an elastic material from the tropoelastin in the solution that does not disperse or dissociate into free tropoelastin; and recovering the elastic material thereby producing the elastic material from the tropoelastin.

2. The process of claim 1, wherein the temperature is greater than about 4° C.

3. The process of claim 1, wherein the temperature is about 37° C.

4. The process of claim 1, wherein the solution of tropoelastin has a salt concentration of less than about 200 mM.

5. The process of claim 4, wherein the salt concentration is greater than about 60 mM and the pH is less than about 10.

6. The process of claim 1, wherein the tropoelastin is present in the solution at a concentration of greater than about 1.5 mg/mL.

7. The process of claim 1, wherein the tropoelastin is present in the solution at a concentration of between about 10 mg/mL and 200 mg/mL.

8. The process of claim 1, wherein the tropoelastin includes a sequence that is the same as or similar to a hydrophilic domain of tropoelastin.

9. The process of claim 1, wherein the tropoelastin consists of a sequence that is the same as or similar to a hydrophilic domain of tropoelastin.

10. The process of claim 1, wherein the elastic material further includes a component selected from the group consisting of pharmaceuticals, biological cells, biological factors, and biological molecules.

11. The process of claim 3, wherein the temperature is less than 42° C.

* * * * *